(12) United States Patent
Ryan et al.

(10) Patent No.: US 6,472,351 B1
(45) Date of Patent: Oct. 29, 2002

(54) HERBICIDE

(75) Inventors: Robert Eugene Ryan, Snetterton (GB); Sandra Morris, Snetterton (GB)

(73) Assignee: Barrier Biotech Limited, Norfolk (GB)

( * ) Notice: Subject to any disclaimer, the term of this patent is extended or adjusted under 35 U.S.C. 154(b) by 0 days.

(21) Appl. No.: 09/646,091

(22) PCT Filed: Mar. 17, 1999

(86) PCT No.: PCT/GB99/00809

§ 371 (c)(1),
(2), (4) Date: Jan. 5, 2001

(87) PCT Pub. No.: WO99/46994

PCT Pub. Date: Sep. 23, 1999

(30) Foreign Application Priority Data

Mar. 17, 1998 (GB) .............................................. 9805670

(51) Int. Cl.$^7$ .............................................. A01N 37/00
(52) U.S. Cl. ...................................................... 504/320
(58) Field of Search .................................. 504/116, 320

(56) References Cited

U.S. PATENT DOCUMENTS 6,051,233 A * 4/2000 Champon ................ 424/195.1

FOREIGN PATENT DOCUMENTS

| JP | 600004598 | * | 1/1985 |
| WO | WO 97 16975 A | | 5/1997 |
| WO | CH 688 787 A | | 3/1998 |

OTHER PUBLICATIONS

S.F. Vaughn & C.F. Spencer, "Volatile monoterpenes as potential parent structures for new herbicides", Weed Science, 1993, XP002107453.

N. Dudai, A. Poljakoff–Mayber, A.M. Mayer, E. Putievsky & H.R. Lerner, "Essential oils as allelochemicals and their potential use as bioherbicides", J. Chem. Ecol., 1999, XP002107454.

Database WPI Section Ch, Week 9214, Derwent Publications Ltd., XP002107455 & JP 04 053563 A, Kurita Water Ind Ltd, Feb. 21, 1992.

Database WPI Section Ch, Week 9028, Derwent Publications Ltd., XP002107456 & JP 02 142703 A, Kurita Water Ind Ltd, May 31, 1990.

* cited by examiner

Primary Examiner—Alton Pryor
(74) Attorney, Agent, or Firm—Bacon & Thomas

(57) ABSTRACT

There is disclosed the use of citronella oil as a herbicide. The citronella oil is provided as a herbicidal composition together with a carrier diluent or excipient therefor. The citronella oil or the herbicidal composition is used to control weeds at a locus by applying thereto a herbicidally effective amount of the citronella oil or the herbicidal composition.

8 Claims, No Drawings

HERBICIDE

The present invention is concerned with a herbicide and, in particular, with the use of an essence oil as a herbicide, as well as a herbicidal composition and a process for controlling growth of unwanted vegetation or weeds.

Previously, standard chemical treatments including hormonal herbicides such as 2, 4-D, a translocated herbicide, were used in controlling weed species, such as for example, common ragwort (Senecio Jacobaea), which is widespread in pastures and which is toxic to livestock. However, such chemicals can generally take 4 to 6 weeks to work and are dependent upon favourable weather conditions for optimum activity.

The inventors of the present invention have surprisingly found that essential oils may be extremely effective as herbicides. The use of essential oils has never previously been disclosed as having a herbicidal effect. The term "essential oils" used in accordance with the present invention refers to compositions comprising a mixture of terpene hydrocarbons and related alcohols, aldehydes and esters.

Therefore, the present invention provides for the use of an essential oil as a herbicide. Advantageously, essential oils, being relatively non-toxic are highly advantageous in terms of their relative ease of application and toxicity profile to non-target organisms.

The essential oil used in accordance with the invention is citronella oil, which may advantageously be included in a herbicidal composition, in an effective amount together with a carrier, diluent or excipient therefor. The major terpene derivative present in citronella oil or citronellol. Terpene compounds and essential oils are significantly more environmentally friendly than previously used agricultural chemicals which have heretofore served as conventional herbicides.

Preferably, the composition comprises the combination of the following ingredients as an approximate percentage of the total composition, 20–30% citronella oil, 5 to 15% surfactant and between 55 to 75% water.

Even more preferably, the herbicidal composition according to the invention comprises 25% essential oil such as citronella oil or the like, 10% surfactant, 65% water or a deviation of plus or minus approximately 10% of said percentage values. Preferably, a bitter of unpalatable compound may be added to the composition so as to render it unpleasant or unpalatable for animal consumption, such as, for example, Bittrex™, or the like.

Improvement in the intensity and speed of action may, advantageously be obtained by, for example, addition of suitable adjuvants to the composition such as for example wetting agents or oils.

The surfactant used in accordance with the present invention is chosen primarily for its function as an emulsifier. Accordingly, any suitable surfactant may be used although preferably an anionic surfactant may be utilised.

The essential oil may be provided in the form of a powder, dust, granules, a solution, emulsion or suspension, with the addition of a liquid and/or solid carriers and/or diluents or the like. Suitable solid carriers include mineral earths, such as for example, bentonite, silica gel, talc, attapulgite, limestone. Therefore, according to a further aspect of the invention there is provided a herbicidal agent comprising citronella oil, or the like, absorbed, dissolved or emulsified into a solid or liquid carrier. Preferably, when the carrier is a solid it can itself dissolve in a liquid carrier, such as water. Thus advantageously the herbicidal agent may be supplied in a convenient storage form and may subsequently be dissolved in a suitable amount of water for subsequent application, by spraying or the like.

The composition may be applied in a manner known to those in the art, for example, with water as the carrier in spray mixture volumes.

According to a further aspect of the invention there is provided a method for controlling the growth of weeds at a locus which method comprises applying thereto an effective amount of citronella oil and more preferably, applying an effective amount of a herbicidal composition or agent according to the invention.

The citronella oil and also the composition used in accordance with the invention has, advantageously, been found to be particularly effective against broad leaved weed species such as docks, nettles and thistles, although it is particularly effective against common ragwort which is toxic to livestock.

The present invention may be more clearly understood with reference to the accompanying examples, which are purely exemplary.

EXAMPLE 1

Laboratory Tests

In April 1996 healthy young bushy ragwort plants were collected from 7 separate locations in and around the Breckland area of Norfolk. Plants were lifted from a variety of soil types, re-potted in the same soil in 2.5 kg pots within 10 minutes of being lifted an then brought back to the lab. Details of the collection points and the locations of all the test sites are outlined in Table 1. The potted plants were left to settle, acclimatise and re-establish themselves for 14 days before being sprayed with a composition according to the invention. These individual potted plants were then rated at intervals using a descriptive scoring system as follows:

| | |
|---|---|
| 0 = No effect | 3 = Very Shrivelled |
| 1 = Wilting | 4 = Completely Shrivelled |
| 2 = Shrivelled | 5 = Completely dead |

Specifically a batch quantity of approximately 5 liters of a herbicidal composition (and which is identified as BH 99 in Tables 2.1 to 2.7) was prepared and which consisted of:

| | | |
|---|---|---|
| 1250 mls | Citronella Oil | (25%) |
| 500 mls | Surfactant | (10%) |
| 3250 mls | Water | (65%) |

Healthy young plants having a leaf spread of from 10–20cm in diameter were removed from various soil types in and around the Breckland area and re-planted in the soil as indicated in Table 1 below:

TABLE 1

| SITE | SOIL TYPE | NO. OF PLANTS | | POSITION |
|---|---|---|---|---|
| 1. Mayday Wood, Near Elvedon | Light sandy gravel | M1 | 30 | Sunny |
| 2. Bradcar Farm, Shropham | Light sandy | B1 | 30 | Sunny |
| 3. Lodge Farm, Thetford | Heavy | L1 | 30 | Sunny/ shade |

TABLE 1-continued

| SITE | SOIL TYPE | NO. OF PLANTS | | POSITION |
|---|---|---|---|---|
| 4. 2, Hillside, Shropham | Light sandy | S1 | 30 | Shade |
| 5. Wretham Heath, Wretham | Medium - Stoney | W1 | 30 | Sunny/Shade |
| 6. O/skirts - Wayland Wood | Medium | W2 | 20 | Sunny/Shade |
| 7. Attleborough - Road Verges | Light sandy/medium | A1 | 30 | Shade |

Position:
Sunny - On open ground - never shaded by plants or trees.
Shade - Partly shaded by plants/trees/buildings.
Sunny/Shade - Dependent upon the sun's position.
note -
Ragwort was difficult to find in heavy soil and in permanent shaded areas.

All the plants were removed carefully so as not to damage the roots and were lifted in such a way as to retain all the surrounding soil. Each plant was re-planted into 2.5 kg. pots within 10 minutes of being lifted.

All the Ragwort was left to settle for a period of fourteen days to ensure that plants that were to be sprayed with the composition were healthy and not affected by replanting.

To observe any effect of the composition it was applied after one hour, one day, 3 days and days after manufacture. Plants were divided into groups of ten. Results of the trials are provided in Tables 2.1 to 2.7.

TABLE A2.1

Efficacy of BH99 against ragwort in laboratory tests (Attleborough).

| Plant Code | Formulation Number | Plant size (cms) | Efficacy Rating 0–5 score (0 = no effect) | | | | | | |
|---|---|---|---|---|---|---|---|---|---|
| | | | 1 hr | 24 hrs | 48 hrs | 72 hrs | 7 days | 14 days | 21 days |
| A1-1 | BHH-001 | 12 | 1 | 2 | 5 | 5 | 5 | 5 | 5 |
| A1-2 | BHH-001 | 12 | 1 | 2 | 5 | 5 | 5 | 5 | 5 |
| A1-3 | BHH-001 | 8 | 1 | 2 | 5 | 5 | 5 | 5 | 5 |
| A1-4 | BHH-001 | 16 | 1 | 2 | 5 | 5 | R* | 5 | 5 |
| A1-5 | BHH-001 | 4 | 1 | 5 | 5 | 5 | 5 | 5 | 5 |
| A1-6 | BHH-001 | 3 | 1 | 5 | 5 | 5 | 5 | 5 | 5 |
| A1-7 | BHH-001 | 12 | 1 | 2 | 5 | 5 | 5 | 5 | 5 |
| A1-8 | BHH-001 | 7 | 1 | 5 | 5 | 5 | 5 | 5 | 5 |
| A1-9 | BHH-001 | 7 | 1 | 5 | 5 | 5 | 5 | 5 | 5 |
| A1-10 | BHH-001 | 6 | 1 | 5 | 5 | 5 | 5 | 5 | 5 |
| A1-11 | BHH-002 | 13 | 1 | 2 | 5 | 5 | 5 | 5 | 5 |
| A1-12 | BHH-002 | 12 | 1 | 2 | 5 | 5 | 5 | 5 | 5 |
| A1-13 | BHH-002 | 18 | 1 | 2 | 5 | 5 | R* | 5 | 5 |
| A1-14 | BHH-002 | 17 | 1 | 2 | 5 | 5 | 5 | 5 | 5 |
| A1-15 | BHH-002 | 13 | 1 | 2 | 5 | 5 | 5 | 5 | 5 |
| A1-16 | BHH-002 | 10 | 1 | 5 | 5 | 5 | 5 | 5 | 5 |
| A1-17 | BHH-002 | 3 | 1 | 5 | 5 | 5 | 5 | 5 | 5 |
| A1-18 | BHH-002 | 6 | 1 | 5 | 5 | 5 | 5 | 5 | 5 |
| A1-19 | BHH-002 | 6 | 1 | 5 | 5 | 5 | 5 | 5 | 5 |
| A1-20 | BHH-002 | 7 | 1 | 5 | 5 | 5 | 5 | 5 | 5 |
| A1-21 | BHH-003 | 16 | 1 | 2 | 5 | 5 | 5 | 5 | 5 |
| A1-22 | BHH-003 | 16 | 1 | 2 | 5 | 5 | 5 | 5 | 5 |
| A1-23 | BHH-003 | 4 | 1 | 5 | 5 | 5 | 5 | 5 | 5 |
| A1-24 | BHH-003 | 7 | 1 | 5 | 5 | 5 | 5 | 5 | 5 |
| A1-25 | BHH-003 | 4 | 1 | 5 | 5 | 5 | 5 | 5 | 5 |
| A1-26 | BHH-003 | 12 | 1 | 2 | 5 | 5 | 5 | 5 | 5 |
| A1-27 | BHH-003 | 10 | 1 | 5 | 5 | 5 | 5 | 5 | 5 |
| A1-28 | BHH-003 | 5 | 1 | 5 | 5 | 5 | 5 | 5 | 5 |
| A1-29 | BHH-003 | 7 | 1 | 5 | 5 | 5 | 5 | 5 | 5 |
| A1-30 | BHH-003 | 18 | 1 | 2 | 5 | 5 | 5 | 5 | 5 |

| No of tests | | Weed size | Efficacy (0–5 Score) | | | | | | |
|---|---|---|---|---|---|---|---|---|---|
| | | | 1 hr | 24 hrs | 48 hrs | 72 hrs | 7 days | 14 days | 21 days |
| 30 | Mean: | 9.7 | 1 | 3.6 | 5 | 5 | 5 | 5 | 5 |
| | Max: | 18 | 1 | 5 | 5 | 5 | 5 | 5 | 5 |
| | Min: | 3 | 1 | 2 | 5 | 5 | 5 | 5 | 5 |

*R Some re-growth at base of plants. Retreated with second application of BH99 to give complete control.

TABLE A2.2

Efficacy of BH99 against ragwort in laboratory tests (Bradcar farm).

| Plant | Formulation | Plant | Efficacy Rating 0–5 score (0 = no effect) |

TABLE A2.2-continued

Efficacy of BH99 against ragwort in laboratory tests (Bradcar farm).

| Code | Number | size (cms) | 1 hr | 24 hrs | 48 hrs | 72 hrs | 7 days | 14 days | 21 days |
|---|---|---|---|---|---|---|---|---|---|
| B1-1 | BHH-001 | 12 | 1 | 2 | 4 | 4 | 5 | 5 | 5 |
| B1-2 | BHH-001 | 13 | 1 | 2 | 4 | 4 | 5 | 5 | 5 |
| B1-3 | BHH-001 | 10 | 1 | 5 | 4 | 4 | 5 | 5 | 5 |
| B1-4 | BHH-001 | 6 | 1 | 5 | 4 | 4 | 5 | 5 | 5 |
| B1-5 | BHH-001 | 13 | 1 | 2 | 4 | 4 | 5 | 5 | 5 |
| B1-6 | BHH-001 | 10 | 1 | 2 | 4 | 4 | 5 | 5 | 5 |
| B1-7 | BHH-001 | 7 | 1 | 5 | 4 | 4 | 5 | 5 | 5 |
| B1-8 | BHH-001 | 8 | 1 | 5 | 4 | 4 | 5 | 5 | 5 |
| B1-9 | BHH-001 | 16 | 1 | 2 | 4 | 4 | 5 | 5 | 5 |
| B1-10 | BHH-001 | 18 | 1 | 2 | 4 | 4 | R* | 5 | 5 |
| B1-11 | BHH-002 | 16 | 1 | 2 | 4 | 4 | 5 | 5 | 5 |
| B1-12 | BHH-002 | 13 | 1 | 2 | 4 | 4 | 5 | 5 | 5 |
| B1-13 | BHH-002 | 6 | 1 | 5 | 4 | 4 | 5 | 5 | 5 |
| B1-14 | BHH-002 | 5 | 1 | 5 | 4 | 4 | 5 | 5 | 5 |
| B1-15 | BHH-002 | 17 | 1 | 2 | 4 | 4 | 5 | 5 | 5 |
| B1-16 | BHH-002 | 13 | 1 | 2 | 4 | 4 | 5 | 5 | 5 |
| B1-17 | BHH-002 | 13 | 1 | 2 | 4 | 4 | 5 | 5 | 5 |
| B1-18 | BHH-002 | 16 | 1 | 2 | 4 | 4 | R* | 5 | 5 |
| B1-19 | BHH-002 | 7 | 1 | 5 | 4 | 4 | 5 | 5 | 5 |
| B1-20 | BHH-002 | 16 | 1 | 5 | 4 | 4 | 5 | 5 | 5 |
| B1-21 | BHH-003 | 12 | 1 | 2 | 5 | 5 | 5 | 5 | 5 |
| B1-22 | BHH-003 | 14 | 1 | 2 | 5 | 5 | 5 | 5 | 5 |
| B1-23 | BHH-003 | 13 | 1 | 2 | 5 | 5 | 5 | 5 | 5 |
| B1-24 | BHH-003 | 6 | 1 | 5 | 5 | 5 | 5 | 5 | 5 |
| B1-25 | BHH-003 | 7 | 1 | 5 | 5 | 5 | 5 | 5 | 5 |
| B1-26 | BHH-003 | 18 | 1 | 2 | 5 | 5 | 5 | 5 | 5 |
| B1-27 | BHH-003 | 12 | 1 | 2 | 5 | 5 | 5 | 5 | 5 |
| B1-28 | BHH-003 | 13 | 1 | 2 | 5 | 5 | 5 | 5 | 5 |
| B1-29 | BHH-003 | 10 | 1 | 2 | 5 | 5 | 5 | 5 | 5 |
| B1-30 | BHH-003 | 8 | 1 | 5 | 5 | 5 | 5 | 5 | 5 |

| | | | Efficacy (0–5 Score) | | | | | | |
|---|---|---|---|---|---|---|---|---|---|
| No of tests | | Weed size | 1 hr | 24 hrs | 48 hrs | 72 hrs | 7 days | 14 days | 21 days |
| 30 | Mean: | 11.63 | 1 | 3.2 | 4.36 | 4.36 | 5 | 5 | 5 |
| | Max: | 18 | 1 | 5 | 5 | 5 | 5 | 5 | 5 |
| | Min: | 5 | 1 | 2 | 4 | 4 | 5 | 5 | 5 |

*R Some re-growth at base of plants. Retreated with second application of BH99 to give complete control.

TABLE A2.3

Efficacy of BH99 against ragwort in laboratory tests (Hillside, Shropham).

| Plant Code | Formulation Number | Plant size (cms) | Efficacy Rating 0–5 score (0 = no effect) | | | | | | |
|---|---|---|---|---|---|---|---|---|---|
| | | | 1 hr | 24 hrs | 48 hrs | 72 hrs | 7 days | 14 days | 21 days |
| S1-1 | BHH-001 | 18 | 1 | 2 | 5 | 5 | 5 | R* | 5 |
| S1-2 | BHH-001 | 20 | 1 | 2 | 5 | 5 | 5 | R* | 5 |
| S1-3 | BHH-001 | 6 | 1 | 5 | 5 | 5 | 5 | 5 | 5 |
| S1-4 | BHH-001 | 7 | 1 | 5 | 5 | 5 | 5 | 5 | 5 |
| S1-5 | BHH-001 | 16 | 1 | 2 | 5 | 5 | 5 | 5 | 5 |
| S1-6 | BHH-001 | 17 | 1 | 2 | 5 | 5 | 5 | 5 | 5 |
| S1-7 | BHH-001 | 12 | 1 | 2 | 5 | 5 | 5 | 5 | 5 |
| S1-8 | BHH-001 | 13 | 1 | 2 | 5 | 5 | 5 | 5 | 5 |
| S1-9 | BHH-001 | i3 | 1 | 2 | 5 | 5 | 5 | 5 | 5 |
| S1-10 | BHH-001 | 12 | 1 | 2 | 5 | 5 | 5 | 5 | 5 |
| S1-11 | BHH-002 | 12 | 1 | 2 | 5 | 5 | 5 | 5 | 5 |
| S1-12 | BHH-002 | 13 | 1 | 2 | 5 | 5 | 5 | 5 | 5 |
| S1-13 | BHH-002 | 7 | 1 | 5 | 5 | 5 | 5 | 5 | 5 |
| S1-14 | BHH-002 | 18 | 1 | 2 | 5 | 5 | R* | 5 | 5 |
| S1-15 | BHH-002 | 8 | 1 | 5 | 5 | 5 | 5 | 5 | 5 |
| S1-16 | BHH-002 | 14 | 1 | 2 | 5 | 5 | 5 | 5 | 5 |
| S1-17 | BHH-002 | 13 | 1 | 2 | 5 | 5 | 5 | 5 | 5 |
| S1-18 | BHH-002 | 10 | 1 | 2 | 5 | 5 | 5 | 5 | 5 |
| S1-19 | BHH-002 | 5 | 1 | 5 | 5 | 5 | 5 | 5 | 5 |
| S1-20 | BHH-002 | 15 | 1 | 2 | 5 | 5 | 5 | 5 | 5 |
| S1-21 | BHH-003 | 13 | 1 | 2 | 5 | 5 | 5 | 5 | 5 |
| S1-22 | BHH-003 | 6 | 1 | 5 | 5 | 5 | 5 | 5 | 5 |
| S1-23 | BHH-003 | 7 | 1 | 5 | 5 | 5 | 5 | 5 | 5 |

EXAMPLE 2

Field Trials

Following the successful results of the lab tests, two un-replicated field tests were organised in July 1996. Two areas of unused grazing land approximately 50×50 meters were selected in Norfolk and each contained 200–250 bushy ragwort plants averaging 10–20 cms in height. Each plant in these areas was well-moistened with approximately 4 mls of spray solution and then observed over the next 4 weeks. Descriptions of the state of the treated plants were recorded at 2 days, 3 days and then at weekly intervals. No untreated areas were left within the test area but untreated ragwort plants were present outside the test area in adjacent parts of the fields. The results of these tests are presented below.

Broadcar Farm—Small Field

This was an area of grazing measuring 50M×50M.

Ragwort was more abundant all over the field. A total of 1L of the herbicidal composition outlined in Example 1 was used to treat 250 plants of various sizes. Sizes were from small bushy plants averaging 10 cm to larger thicker stem plants averaging 20 cm.

Application was started at 9 am and finished at 2.30 pm. Average temperature was 20c. Conditions were wet overnight turning dry and sunny.

Plants were sprayed at close range (approx. 20 cm) and well moistened. At 2.30 pm the plants were observed that were sprayed at 9 am and it was noted the plants were already dying having wilted considerably—the stems were completely bent over whilst the plants were spread flat on the ground.

Day Two

All plants had wilted and were no longer upright.

Day Three

The plants were turning dark in colour and were wilted and flat to the ground.

Week One

The plants were completely destroyed and easily pulled up with the root intact. The root assembled a dark rubber material and was limp and dead.

Week Two

Four plants had small re-growths at the base of the dead stem. The herbicidal composition was re-applied and left for 48 hours. By day three the re-growth had completely died.

Week Three

No recovery was observed.

Week Four

No recovery was observed.

Hillside Cottage—Shropham

This was an area of grazing measuring 50M×50M.

Ragwort was more abundant along the bottom end of the field. A composition according to Example 1—a total of 800 mls was used to treat 200 plants of various sizes. Sizes were from small bushy plants averaging 10 cm to larger thicker stem plants averaging 20 cm.

Application was started at 9 am and finished at 2 pm. Average temperature was 22c. Conditions were slight dampness first thing turning dry and sunny.

Plants were sprayed at close range (approx. 20 cm) and well moistened. At 2 pm the plants were observed that were sprayed at 9 am and it was noted that the plants were already dying having wilted considerably—the stems were completely bent over and the plants were spread flat on the ground.

Day Two

All plants had wilted and were no longer upright.

Day Three

The plants were turning dark in colour and were wilted and flat to the ground.

Week One

The plants were completely destroyed and easily pulled up with the root intact. The root resembled a dark rubber material and was limp and dead.

Week Two

No recovery was observed.

Week Three

No recovery was observed.

Week Four

No recovery was observed.

EXAMPLE 3

In 1997 properly replicated field evaluations of the efficacy of the composition according to the invention as a herbicide were carried out and 3 trial sites were located where the composition was tested against the standard product, 2, 4-D applied at a dose of 3.0 l/ha to individual plants. The trials were designed as a randomised complete block but within each "plot" area, 10 ragwort plants for each growth stage (rosette & flowing stems) were tagged with numbered markers and these were treated with the appropriate compound. Single rates of composition were achieved with four squirts of the applicator used (see below) and then plots requiring double doses were treated with a second application of four squirts once all plants in the plot had been treated. This method reduced the risk of excessive run-off if eight squirts had been applied in a single application. Treatments were assessed for efficacy at 1, 7, 14 and 28 days after application using a 0–10 score where 0=no effect and 10=complete kill. The results of these three trials are presented in Tables A4.1 to A4.3 below. As with the larger plants in the laboratory tests, some degree of re-growth was noted on a few of the treated plants. After the last assessments had been made, some of these plants were retreated with a second application of BH 99 and the effect was compared with untreated plants after a further 4 weeks which data is presented in the results section below.

Application Methods

In all evaluations the composition BH 99 was used comprising:

| | | |
|---|---|---|
| 1250 mls | Citronella Oil | (25%) |
| 500 mls | Surfactant | (10%) |
| 3250 mls | Water | (65%) |
| .5 mls | Bittrex | (2 drops) | was applied to plants using the same equipment. The ready-mixed formulated product was contained in a 5 liter polyethylene bottle to which was fitted with a Frapak CHS-5A trigger sprayer and dip tube. This equipment delivers 2.4 mls of spray for each full squeeze of the trigger and provides a very convenient method of application.

In the replicated field trials in 1997, the 2, 4-D treatments were applied using a Hardy (backpack) small plot sprayer fitted with a lance carrying a single F110-03 nozzle. Individual plants were sprayed at a forward speed of 1.6 m/s and a pressure of 2 bar to give an application volume of 200 l/ha. Dose of 2, 4-D applied by this method was 3.0 l/ha.

Results

Laboratory Tests: The results of the laboratory tests of Example 1 are given in Tables A2.1–A2.7 with each table presenting the data on weeds collected from one site.

Each table shows the efficacy of three different preparations of BH 99 the composition used in Examples 1 to 3. BHH-001 was prepared 60 days before application, BHH-002 was prepared 30 days before application and BHH-003 was prepared on the day of application to confirm the stability of the efficacy. The activity was consistent across the range of plant sizes treated with wilting evident after 1 hour, variable shrivelling after 24 hours and plant death after 48 hours. This activity was irrespective of the age of the preparation or the size of the treated plant but in almost every batch of 10 plants, one or two exhibited a degree of re-growth at the base of the plant. These plants tended to be the biggest plants in the batch (16–18 cms) and in every case a second application of BH 99 achieved complete plant death.

In summary, these laboratory tests involved application to 210 individual plants at sizes ranging 3–18 cms. All plants appeared dead within 48 hours of treatment. Re-growth was noted in 18 of the treated plants (8.6% of the population) but 100% control was achieved of all plants when those exhibiting re-growth were given a second dose.

Un-replicated Field Tests: These tests were conducted in areas measuring 50×50 m at Bradcar Farm and Hillside Cottage and a summary of the results is given in Example 2. At Bradcar Farm, 1.0 liters of BH 99 was applied to 250 ragwort plants ranging in size from 10–20 cms tall. Within 24 hours of application all the treated plants were seen to be wilting and all were dead by 7 DAT (days after treatment). At 14 DAT, 4 of the treated ragwort plants displayed signs of re-growth at the base of the treated stems and these were given a second application. The re-growth was noted as dead 3 days after the second application and no recovery or re-growth was observed on any of the treated plants at 21 or 28 DAT. Plants outside the treated area remained healthy.

At Hillside Cottage site, 200 plants in an area 50×50 m were treated with a total of 800 mls of BH 99. Size at application was also 10–20 cms, wilting of all stems was seen at 1 DAT and all ragwort plants were dead by 7 DAT. Observations at 14, 21 and 28 DAT recorded no re-growth recovery from any of the treated plants.

Replicated Field Trials, 1997: The efficacy of BH 99 was tested against ragwort at the rosette and flowering stages at Shropham and Barnham sites but only against the rosette stage at Hockham since no flowering stems were presented. The results of the 0–10 scores at these sites are presented in Tables A4.1–A4.3 (10=complete plant death) but the means across sites are summarised in the following tables:

Mean Score for Ragwort Control When Treated at the Rossette Stage:

| Treatment n = 3 | 1 DAT | 7 DAT | 14 DAT | 28 DAT | 42 DAT |
|---|---|---|---|---|---|
| T1 1N BH 99 | 9.0 | 9.5 | 7.2 | 4.8 | 3.7 |
| 2N BH 99 | 9.8 | 10 | 9.5 | 8.8 | 7.5 |
| 3.0 1/ha 2,4-D | 0.1 | 0.5 | 2.1 | 6.9 | 9.4 |
| T2 1N BH 99 | 9.6 | 9.5 | 9.3 | 8.4 | — |
|  | 9.8 | 10 | 9.9 | 9.8 | — |

Mean Score for Ragwort Control When Treated at the Flowering Stage:

| Treatment n = 2 | 1 DAT | 7 DAT | 14 DAT | 28 DAT | 42 DAT |
|---|---|---|---|---|---|
| T1 1N BH 99 | 4.1 | 6.2 | 7.0 | 8.0 | 8.9 |
| 2N BH 99 | 7.3 | 7.7 | 8.9 | 7.9 | 7.5 |
| 3.0 1/ha 2,4-D | 0.3 | 0.8 | 4.9 | 7.4 | 8.4 |
| T2 1N BH 99 | 6.6 | 8.9 | 9.1 | 8.8 | — |
|  | 9.0 | 9.6 | 9.8 | 9.4 | — |

These results show that BH 99 is much quicker acting than 3.0 l/ha 2, 4-D amine but that control tends to degrade towards the end of the assessment period. This was due to fresh growth sprouting from the base of some of the treated stems and the effect of re-treatment is discussed below. This re-growth has been noted in several of the earlier tests but, perhaps of more interest, it is clear that the T2 applications to both rosette and flowering stems were more effective than the Ti applications. The difference between the two timings was merely a 10–13 day delay in the application date in an attempt to get different climatic conditions. The mean air temperature, cloud cover and air humidity are summarised in the next table.

Climatic Conditions at Time of Spraying:

|  | Air Temp ° C. | Cloud Cover (⅛'s) | % Air humidity |
|---|---|---|---|
| T1 | 22.3 | 5.0 | 64.3 |
| T2 | 19 | 7.3 | 73.3 |

This indicates that the T2 application was made under cooler conditions with less direct light and moister air. This may explain the difference in the activity seen but under normal usage, most owners of pasture would not wait until July/August to treat and would be applying the product in Spring when rosettes would be smaller. However, even under these conditions, the T2 application gave broadly similar control to the standard product, 3.0 l/ha 2, 4-D and achieved this level of activity within 7 days of application. The full activity of 2, 4-D was not manifest until 42 days after application.

As stated, the reason for the apparent decline in control by BH 99 was due to re-growth on a number of treated plants. In the lab tests and un-replicated trials a second application of BH 99 had always achieved complete control and so a second application was also made to a representative number o the re-growing plants in these trials. The results of this re-treatment are summarised in the following table 5 together with conditions at application. Plants were scored using a 0–10 scale where 0=no effect and 10=complete plant death as per the earlier assessments.

TABLE 5

Summary of Re-growth Control and Climatic Conditions at Re-treatment

|  | Shropham | Hockham | Barnham |
|---|---|---|---|
| No of plants treated: | 12 | 10 | 9 |
| Efficacy at 7 DAT | 9.5 | 10 | 10 |
| Efficacy at 28 DAT | 3.6 | 5.0 | 10 |
| Air Temp | 23 | 20 | 20.5 |
| Cloud Temp | ⅘ | ⅖ | ⅖ |
| Air humidity | 48% | 66% | 70% |

This data is consistent with a link between environmental conditions and eventual efficacy. Once again the site experiencing around 70% humidity is giving complete control whilst those experiencing dryer conditions show initially good efficacy but eventually show a degree of re-growth. Those experiencing the driest conditions show the greatest re-growth.

The Composition Applied: BH 99, has given complete control of 660 ragwort plants in lab and un-replicated field trials and comparable control to the standard treatment, 2,4-D amine in 3 replicated field trials. Ragwort is a toxic species and a serious pest of pasture and other grassy areas. The composition according to the invention offers an alternative method of controlling this noxious weed, which composition is easy to apply and in addition, being composed of food-grade oils, is likely to be non-toxic to most wildlife.

What is claimed is:

1. A herbicidal composition consisting essentially of by volume approximately from 20 to 30% citronella oil, 5 to 15% surfactant, and from 55 to 75% water.

2. A composition according to claim 1 consisting essentially of by volume approximately 25% citronella oil, 65% water and 10% surfactant.

3. A herbicidal agent consisting essentially of a composition according to any of claim 1 or 2 absorbed, dissolved or emulsified onto a solid or liquid carrier.

4. A herbicidal agent consisting essentially of a composition according to claim 2 absorbed, dissolved or emulsified onto a solid or liquid carrier.

5. A composition according to claim 1 which is further diluted in 1:1 ratio with water.

| A4.2: Barrier Hygiene Ragwort Trial (0–10 Score, 0 = No Control) | | | | | | | | | | | |
|---|---|---|---|---|---|---|---|---|---|---|---|
| Hockham | 25/07/97 | T1 + 1 26/07/97 | T1 + 7 01/08/97 | T1 + 14 07/08/97 | T1 + 28 19/08/97 | T1 + 42 02/09/97 | 04/08/97 | T2 + 1 05/08/97 | T2 + 7 12/08/97 | T2 + 14 22/08/97 | T2 + 28 02/09/97 |
| Rosette: | | | | | | | | | | | |
| Untreated | 1 | 0 | 0 | 0 | 0 | 0 | | 0 | 0 | 0 | 0 |
| 1N BH 99 | 2 | 9 | 9.5 | 8.1 | 5.9 | 2 | | — | — | — | — |
| 2N BH 99 | 3 | 97 | 10 | 10 | 10 | 8.1 | | — | — | — | — |
| l/ha 2,4-D | 4 | 0.1 | 0.4 | 0.8 | 5.2 | 9.8 | | — | — | — | — |
| 1N BH 99 | 5 | — | — | — | — | — | | 9.2 | 9.9 | 9.5 | 8.4 |
| 2N BH 99 | 6 | — | — | — | — | — | | 9.7 | 10 | 10 | 10 |
| Flower: | | | | | | | | | | | |
| Untreated | 1 | 0 | 0 | 0 | 0 | 0 | | 0 | 0 | 0 | 0 |
| 1N BH 99 | 2 | | Not Present at this site | | | | | — | Not Present at th | | — |
| 2N BH 99 | 3 | | | | | | | — | — | — | — |
| l/ha 2,4-D | 4 | | | | | | — | — | — | — | — |
| 1N BH 99 | 5 | — | — | — | — | — | | | | | |
| 2N BH 99 | 6 | — | — | — | — | — | | | | | |
| | | | | 25/07/97 | | | | | 04/08/97 | | |
| | | Air Temp. | | 19 | | | | | 19 | | |
| | | Cloud | | 7 | | | | | 7 | | |
| | | Humidity | 65% | | | 73% | | | | | |

| A4.2: Barrier Hygiene Ragwort Trial (0–10 Score, 0 = No Control) | | | | | | | | | | | |
|---|---|---|---|---|---|---|---|---|---|---|---|
| Barnham | 23/07/97 | T1 + 1 24/07/97 | T1 + 7 30/07/97 | T1 + 14 08/08/97 | T1 + 28 19/08/97 | T1 + 42 02/09/97 | 04/08/97 | T2 + 1 05/08/97 | T2 + 7 12/08/97 | T2 + 14 22/08/97 | T2 + 28 02/09/97 |
| Rosette: | | | | | | | | | | | |
| Untreated | 1 | 0 | 0 | 0 | 0 | 0 | | 0 | 0 | 0 | 0 |
| 1N BH 99 | 2 | 8.7 | 9.4 | 6.4 | 3.5 | 4.5 | | — | — | — | — |
| 2N BH 99 | 3 | 10 | 10 | 9 | 8 | 7 | | — | — | — | — |
| l/ha 2,4-D | 4 | 0.1 | 0.8 | 4.8 | 9.1 | 9.9 | | — | — | — | — |
| 1N BH 99 | 5 | — | — | — | — | — | | 9.8 | 10 | 9.5 | 9.4 |
| 2N BH 99 | 6 | — | — | — | — | — | | 9.8 | 9.9 | 10 | 10 |
| Flower: | | | | | | | | | | | |
| Untreated | 1 | 0 | 0 | 0 | 0 | 0 | | 0 | 0 | 0 | 0 |
| 1N BH 99 | 2 | 4.8 | 6.3 | 7.7 | 8.6 | 9.7 | | — | — | — | — |
| 2N BH 99 | 3 | 6.7 | 7.3 | 8.3 | 9.3 | 8.4 | | — | — | — | — |
| l/ha 2,4-D | 4 | 0.3 | 1 | 7.3 | 8.9 | 9.4 | | — | — | — | — |
| 1N BH 99 | 5 | — | — | — | — | — | | 7 | 9.1 | 9.6 | 8.9 |
| 2N BH 99 | 6 | — | — | — | — | — | | 9.2 | 10 | 10 | 9.5 |
| | | | | 23/07/97 | | | | 04/08/97 | | | |
| | | Air Temp. | | 26 | | | | 19 | | | |
| | | Cloud | | 5 | | | | 8 | | | |
| | | Humidity | 71% | | | 74% | | | | | |

6. A method for controlling the growth of ragwort, docks, nettles or thistles at a locus which method comprises applying thereto a herbicidally effective amount of citronella oil.

7. A method according to claim 6 which comprises applying a herbicidally effective amount of a composition consisting essentially of by volume approximately from 20 to 30% citronella oil, 5 to 15% surfactant, and from 55 to 75% water.

8. A method according to claim 6 which comprises applying a herbicidally effective amount of a composition comprising by volume approximately from 25% citronella oil, 65% water and 10% surfactant.

* * * * *